US00PP34470P2

(12) United States Plant Patent
von Tubeuf

(10) Patent No.: US PP34,470 P2
(45) Date of Patent: Aug. 2, 2022

(54) POINSETTIA PLANT NAMED 'NPCW20347'

(50) Latin Name: *Euphorbia pulcherrima*
Varietal Denomination: 'NPCW20347'

(71) Applicant: KLEMM + SOHN GMBH & CO. KG, Stuttgart (DE)

(72) Inventor: Guido von Tubeuf, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/573,776

(22) Filed: Jan. 12, 2022

(51) Int. Cl.
*A01H 5/12* (2018.01)

(52) U.S. Cl.
USPC ..... Plt./307

(58) Field of Classification Search
USPC ..... Plt./302, 303, 307
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new poinsettia plant particularly distinguished by having a late earliness, high vigor and dark bract color, is disclosed.

1 Drawing Sheet

Genus and species: *Euphorbia pulcherrima.*
Variety denomination: 'NPCW20347'.

BACKGROUND OF THE NEW PLANT

The present invention comprises a new and distinct variety of poinsettia, botanically known as *Euphorbia pulcherrima* and hereinafter referred to by the variety name 'NPCW20347'. 'NPCW20347' is a selection from a cross-pollination conducted in December 2014 in Nairobi, Kenya of the commercial female *Euphorbia* line 'Vesuvio' (unpatented) and the commercial male *Euphorbia* line 'NPCW14221' (U.S. Plant Pat. No. 27,135). Seeds from the cross were selected and plants were grown for evaluation. A plant line was selected in October 2015 and grafting took place from the selection in March 2016 in Stuttgart, Germany and named 'NPCW20347'. In May 2016, 'NPCW20347' was first vegetatively propagated by apical cuttings. 'NPCW20347' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. Late earliness;
2. High vigor; and
3. Dark bract color.

DESCRIPTION OF THE PHOTOGRAPH

This new poinsettia plant is illustrated by the accompanying photograph which shows an overall view of the plant. The photograph is of a plant approximately thirteen-weeks-old grown indoors Stuttgart, Germany in December 2018. The colors shown are as true as can be reasonably obtained by conventional photographic procedures.

DESCRIPTION OF THE NEW VARIETY

The following detailed descriptions set forth the distinctive characteristics of 'NPCW20347'. The data which define these characteristics were collected from asexual reproductions carried out in Stuttgart, Germany. Data was collected on nineteen-week-old plants grown indoors in Stuttgart, Germany under greenhouse conditions in December of 2021. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW20347'.

Parentage:
- *Male.*—*Euphorbia* line 'NPCW14221' (U.S. Plant Pat. No. 27,135).
- *Female.*—*Euphorbia* line 'Vesuvio' (unpatented).

Plant:
- *Form.*—Triangular.
- *Growth habit.*—Upright.
- *Height.*—32.0 cm to 35.0 cm.
- *Width.*—27.0 cm to 31.0 cm.
- *Average number of inflorescences per plant.*—5 to 6.
- *Keeping quality.*—Very good.
- *Time to produce a cutting.*—5 weeks.
- *Blooming habit.*—Intermittent.
- *Flowering response time.*—Approximately 60 days.

Propagation:
- *Type cuttings.*—Apical cuttings.
- *Time to produce a rooted cutting.*—4 weeks.
- *Rooting habit and root color.*—Freely branching and white.

Lateral branches:
- *Color.*—RHS 143A.
- *Length.*—29.0 cm to 32.0 cm.
- *Internode length.*—1.5 cm to 4.0 cm.
- *Diameter.*—0.5 cm to 0.8 cm.
- *Branching habit.*—Freely branching.
- *Number of lateral branches per plant.*—5 to 6.
- *Texture.*—Smooth.
- *Strength.*—Strong.

Leaves:

*Quantity.*—7 to 10 per lateral branch.

*Arrangement.*—Alternate.

*Number of lobes on the leaf blade.*—2 to 4.

*Lobation depth.*—Shallow.

*Depth of the deepest sinus of the leaf blade.*—0.5 cm.

*Shape.*—Ovate.

*Apex.*—Acute.

*Base.*—Obtuse.

*Margin.*—Slightly serrate, some leaves entire.

*Length.*—9.0 cm to 16.0 cm.

*Width.*—6.0 cm to 9.0 cm.

*Texture* (*both surfaces*).—Smooth.

*Vein color.*—Upper surface: Transparent. Lower surface: RHS 139D, main vein slightly reddish midvein of RHS 35C.

*Variegation.*—Absent.

*Venation pattern.*—Reticulate.

*Color.*—Mature foliage: Upper surface: RHS 139A. Lower surface: RHS 139D. Immature foliage: Upper surface: RHS 141A. Lower surface: RHS 139B.

*Leaf petiole.*—Length: 3.0 cm to 6.0 cm. Diameter: 0.2 cm to 0.3 cm. Color: Upper (part) surface: RHS 59A. Lower (part) surface: RHS 181A. Texture: Smooth. Strength: Medium. Transitional leaves: Sparse. Shape: Ovate. Length: 8.0 cm to 10.0 cm. Width: 5.0 cm to 7.0 cm. Color: Upper surface: RHS 141A and RHS 46A. Lower surface: RHS 139B and RHS 47A.

Inflorescence:

*Type and habit.*—Cluster of cyathia surrounded by bracts.

*Quantity per lateral branch.*—1.

*Position relative to foliar plane.*—Above.

*Lastingness of inflorescence on the plant.*—Two months.

*Natural flowering season.*—November and December.

*Diameter.*—20.0 cm to 25.0 cm.

*Height.*—3.0 cm to 4.0 cm.

*Fragrance.*—Absent.

Bracts:

*Number of bracts per inflorescence.*—6 to 8.

*Shape.*—Ovate.

*Apex.*—Acute.

*Base.*—Obtuse.

*Margin.*—Mostly entire, older bracts slightly serrate.

*Size.*—Length: 9.0 cm to 13.0 cm. Width: 5.0 cm to 7.0 cm.

*Texture* (*both upper and lower surfaces*).—Smooth.

*Folding along the main vein.*—Absent.

*Twisting.*—Absent.

*Rugosity between the veins.*—Absent.

*Venation pattern.*—Reticulate.

*Vein color.*—Upper surface: RHS 59A. Lower surface: RHS 181A.

*Bract color.*—Upper surface: Closest to RHS 46A. Lower surface: Closest to RHS 47A.

*Bract petiole.*—Length: 0.5 cm to 2.5 cm. Diameter: 0.2 cm to 0.3 cm. Color: Upper (part) surface: RHS 59A. Lower (part) surface: RHS 181A. Texture: Smooth. Strength: Medium.

Cyme:

*Diameter.*—1.0 cm to 2.5 cm.

*Cyathia number.*—7.0 cm to 10.0 cm per inflorescence.

*Deformation of glands of the cyathium.*—Absent.

*Timing of opening of cyathia.*—Beginning of December; first pollen appears in parallel to opening of the nectar cups, stigmas appear 2 weeks later.

*Cyathium.*—Shape: Ovate. Texture: Smooth. Diameter: 0.2 cm to 0.5 cm. Length: 0.3 cm to 0.7 cm. Color: RHS 142B.

*Peduncle.*—Color: RHS 142B. Length: 0.2 cm to 0.3 cm. Diameter: 0.1 cm. Texture: Smooth. Strength: Medium.

*Nectar cups.*—Number: 1 per cyathium. Diameter: 0.1 cm. Length: 0.4 cm to 0.6 cm. Color: RHS 13B. Shape: Lip shaped. Texture: Smooth.

Reproductive organs:

*Stamen quantity.*—10 to 15 per cyathium.

*Stamen shape.*—Ovate.

*Filament length.*—0.3 cm.

*Filament color.*—RHS 39A.

*Pollen quantity.*—Sparse.

*Pollen color.*—RHS 6A.

*Gynoecium.*—Present. Pistil quantity per cyathium: 1. Pistil length: 0.2 cm. Stigma form: Divided in 2 parts. Stigma color: RHS 183A. Style length 0.2 cm. Style color: RHS 183A. Ovary length: 0.05 cm. Ovary color: RHS 143C.

Fruit and seed set: Not observed.

Disease and insect resistance: No particular disease or insect resistance observed.

COMPARISON WITH PARENTAL LINE AND KNOWN VARIETY

'NPCW20347' is distinguished from its mutation parent as described in Table 1:

TABLE 1

Comparison with Parental Lines

| Trait or characteristic | Instant variety NPCW20347 | Female parent Vesuvio | Male Parent NPCW14221 |
|---|---|---|---|
| Earliness | Late (resp. 60 days) | Early (resp. 50 days) | Late (resp. 57 days) |
| Vigour | High | High | Medium |
| Bract colour | Dark | Brilliant orange red | Medium red |

COMPARISON WITH SIMILAR VARIETY

'NPCW20347' is most similar to the commercial poinsettia plant named 'Grande Italia' (patent status unknown). Differences between the two varieties are described in Table 2:

TABLE 2

| Trait | Variety 'NPCW20347' | Commercial line 'Grande Italia' |
|---|---|---|
| Response time (opening of cyathia) | Later | Earlier (5-7 days) |
| Bract width | Wider | Less wide |
| Stem strength of lateral shoots | Very strong (diameter) | Less strong |

I claim:

1. A new and distinct variety of poinsettia plant named 'NPCW20347' as shown and described herein.

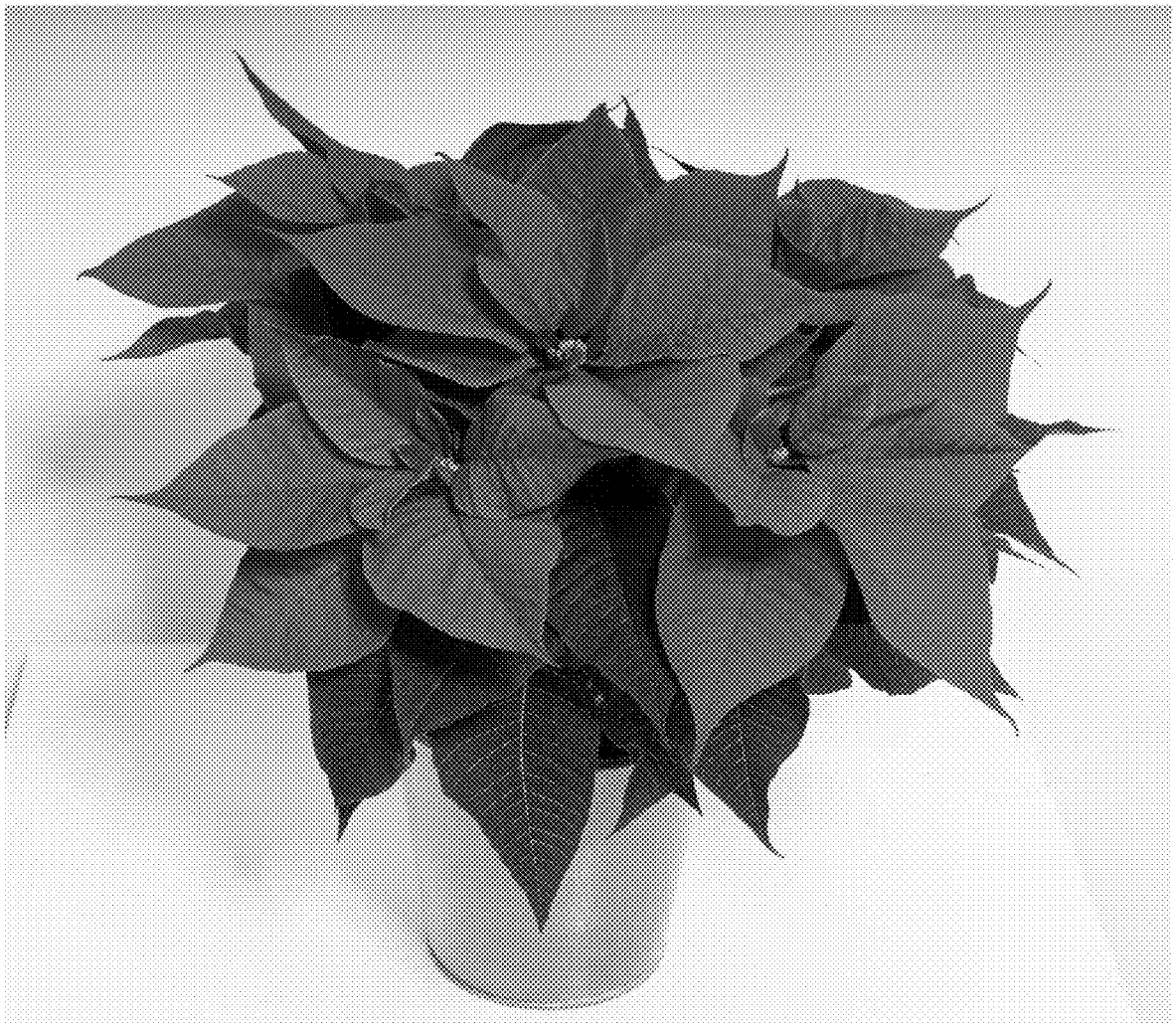

* * * * *